United States Patent
Nishimi et al.

(10) Patent No.: US 7,348,458 B2
(45) Date of Patent: Mar. 25, 2008

(54) PHOSPHONIUM SALT, ORGANICALLY MODIFIED LAYERED SILICATE CONTAINING THE PHOSPHONIUM SALT AND COMPOSITION THEREOF

(75) Inventors: Taisei Nishimi, Minami-ashigara (JP); Koki Nakamura, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 574 days.

(21) Appl. No.: 10/807,163

(22) Filed: Mar. 24, 2004

(65) Prior Publication Data
US 2004/0220309 A1     Nov. 4, 2004

(30) Foreign Application Priority Data
Mar. 28, 2003     (JP)     ............................. 2003-090670

(51) Int. Cl.
*C07F 9/54* (2006.01)
(52) U.S. Cl. ........................................................ 568/9
(58) Field of Classification Search ..................... None
See application file for complete search history.

(56) References Cited

U.S. PATENT DOCUMENTS 4,359,596 A * 11/1982 Howard et al. ............. 585/856

* cited by examiner

*Primary Examiner*—Yvonne Eyler
*Assistant Examiner*—Yevgeny Valenrod
(74) *Attorney, Agent, or Firm*—Sughrue Mion, PLLC

(57) ABSTRACT

A tetraalkylphosphonium salt having at least one branched alkyl chain containing 9 to 100 carbon atoms in total, an organically modified layered silicate containing the tetraalkylphosphonium salt having at least one branched alkyl chain containing 9 to 100 carbon atoms in total between layers of a layered silicate and a composition comprising the organically modified layered silicate and an organic solvent or a thermoplastic resin. There are provided a tetraalkylphosphonium salt for a layered silicate having thermal stability and dispersibility superior to those of conventional organophilized layered silicates, an organically modified layered silicate containing the tetraalkylphosphonium salt and a composition thereof.

9 Claims, No Drawings

PHOSPHONIUM SALT, ORGANICALLY MODIFIED LAYERED SILICATE CONTAINING THE PHOSPHONIUM SALT AND COMPOSITION THEREOF

BACKGROUND OF THE INVENTION

1. Field of the Invention

The present invention relates to a novel phosphonium salt, an organically modified layered silicate organophilized with the phosphonium salt and a composition thereof. More precisely, the present invention relates to a novel phosphonium salt having both of superior interfacial chemical characteristics and superior thermal stability, an organically modified layered silicate organophilized with the phosphonium salt and a composition thereof.

The present invention relates to the field of materials of polymer composites which can exhibit their performance by addition of the aforementioned phosphonium salt, the aforementioned organically modified layered silicate or a composition thereof, including packaging materials of foods, pharmaceutical preparations etc., flame retardant materials used as members of buildings, electric equipments, automobiles etc., viscosity modifiers, additives in cosmetics etc., coating agents, fibers and so forth.

2. Description of the Background

Onium compounds having a long-chain alkyl group are conventionally known to function as cationic surfactants. Among these, quaternary ammonium salts are widely used as cationic surfactants in practice. For example, such quaternary ammonium salts are widely used as surfactants such as those used in hair conditioners and softeners, organophilizing agents for exchanging inorganic cations existing between layers of layered silicates such as bentonite and montmorillonite for quaternary ammonium salts.

It is known that a molecular structure of a surfactant significantly affects surface activity and molecular aggregate structure, and this is systematically explained on the basis of hydrophilic/lipophilic balance of the surfactant. That is, a quaternary ammonium salt having one long-chain alkyl group has hydrophilicity stronger than lipophilicity and therefore forms micelles in water. On the other hand, a quaternary ammonium salt having two long-chain alkyl groups has balanced hydrophilicity and lipophilicity and therefore forms lamellar liquid crystals or bilayer membrane vesicles in water.

Further, it is also known that a difference in molecular structure of a cationic surfactant significantly affects dispersing characteristic of an "organically modified layered silicate" obtained by exchanging inorganic cations in a layered silicate for the cationic surfactant. Therefore, examples of use of a quaternary ammonium salt having a branched alkyl group in a layered silicate as an organophilizing agent have been reported so far, which direct attentions to the difference in the molecular structure (refer to Japanese Patent Laid-open Publication (Kokai) No. 9-309720 (page 2, claim 1, page 3, paragraph [0006] to page 4, paragraph [0012]), for example). In this document, it has been reported that an organically modified layered silicate organophilized with a quaternary ammonium salt having a branched alkyl group exhibited more favorable dispersibility in an organic solvent and thermoplastic resin compared with an organically modified layered silicate organophilized with a quaternary ammonium salt having a straight alkyl group.

However, the aforementioned organically modified layered silicate using a quaternary ammonium salt as an organophilizing agent has a problem that when it is melt-kneaded with a thermoplastic resin at a temperature of 200° C. or higher, the quaternary ammonium salt is decomposed into a tertiary amine and olefin by the Hofmann elimination (or Hofmann degradation) and hence cannot function as an organophilizing agent. The aforementioned organically modified layered silicate organophilized with a quaternary ammonium salt also has a problem that when it is dispersed in an organic solvent and used as grease, the quaternary ammonium salt is thermally decomposed under a high temperature condition of 200° C. or higher (condition of heating site such as bearing of motor) and hence cannot be used under such a condition.

Further, the aforementioned problem of the thermal decomposition of quaternary ammonium salt is also observed in use of quaternary ammonium in the field of semiconductor nanoparticle synthesis by the hot soap method, for example. That is, since the reaction in the hot soap method is performed at a high temperature of 250 to 300° C., the quaternary ammonium salt is thermally decomposed under such a condition and therefore cannot be used as cationic protective colloid.

Quaternary phosphonium salts can be mentioned as oniums having superior thermal stability as compared with quaternary ammonium salts, and in particular, tetraalkylphosphoniums have superior thermal stability. Functions of tetraalkylphosphoniums having such a characteristic have been investigated from various viewpoints, and it has been revealed that they can be applied to phase transfer catalysts, antibacterial agents, thermotropic liquid crystal (A. W. Herriott, D. Picker, "Journal of the American Chemical Society", 97, 2345-2349 (1975); A. Kanazawa et al., "Journal of Polymer Science", Part A: Polymer Chemistry, 31, 3003-3011 (1993); and D. J. Abdallah et al., "Journal of the American Chemical Society", 122, 3053-3062 (2000), for example) and so forth.

However, in all of these documents, straight tetraalkylphosphonium salts and ammonium salts are compared as surfactants, and none of them discloses dispersibility attributable to their molecular structures. Furthermore, none of these documents discloses applicability of tetraalkylphosphonium salts as heat resistant surfactants or organophilizing agents, either.

Therefore, development of cationic surfactants having surface activity and thermal stability comparable or superior to those of quaternary ammonium salts and organically modified layered silicates having superior thermal stability and dispersibility has been desired.

SUMMARY OF THE INVENTION

The present invention was accomplished in view of the aforementioned problems, and an object of the present invention is to provide a novel tetraalkylphosphonium salt having surface activity comparable or superior to that of conventional cationic surfactants as well as both of thermal stability and dispersibility. Further, another object of the present invention is to provide an organically modified layered silicate containing a novel tetraalkylphosphonium salt as an organophilizing agent and a composition containing such an organically modified layered silicate.

The inventors of the present invention systematically synthesized compounds having different alkyl groups for tetraalkylphosphonium salts exhibiting higher thermal stability compared with conventional quaternary ammonium salts and examined surface activity and thermal stability of the compounds. At the same time, they assiduously studied about dispersibility of layered silicates organophilized with these compounds in an organic solvent or thermoplastic resin. As a result, they accomplished the present invention.

That is, the first object of the present invention is achieved by the following tetraalkylphosphonium salt:

(1) A phosphonium salt having at least one branched alkyl chain containing 9 to 100 carbon atoms in total.
(2) The tetraalkylphosphonium salt according to (1), wherein the branched alkyl chain is a branched alkyl chain containing 12 to 50 carbon atoms in total.
(3) The tetraalkylphosphonium salt according to (1), wherein the branched alkyl chain is a branched alkyl chain containing 16 to 36 carbon atoms in total.
(4) The tetraalkylphosphonium salt according to any one of (1) to (3), wherein the branched alkyl chain is branched at the 2-position.
(5) The tetraalkylphosphonium salt according to any one of (1) to (4), which has only one branched alkyl chain.
(6) The tetraalkylphosphonium salt according to any one of (1) to (5), wherein all of alkyl chains except for the branched alkyl chain contain 4 or more carbon atoms in total.
(7) The tetraalkylphosphonium salt according to any one of (1) to (6), wherein all of alkyl chains except for the branched alkyl chain are n-butyl groups.
(8) The tetraalkylphosphonium salt according to any one of (1) to (7), wherein the branched alkyl chain is 2-hexadecylicosyl group.

The tetraalkylphosphonium salt of the present invention has surface activity and thermal stability comparable or superior to those of conventional quaternary ammonium salts. Therefore, the tetraalkylphosphonium salt of the present invention can be used as a cationic surfactant even under a high temperature condition of 200° C. or higher.

Further, the second object of the present invention is achieved by the following organically modified layered silicate.

(1) An organically modified layered silicate containing the aforementioned tetraalkylphosphonium salt between layers of a layered silicate.
(2) The organically modified layered silicate according to (1), which contains 0.05 to 3 molar equivalents of the aforementioned tetraalkylphosphonium salt with respect to 1 molar equivalent of inorganic ions contained in the layered silicate.

The organically modified layered silicate of the present invention contains a tetraalkylphosphonium salt having at least one branched alkyl chain containing 9 to 100 carbon atoms in total. Therefore, since inorganic cations existing between layers of a layered silicate can be exchanged for the tetraalkylphosphonium salt in the organically modified layered silicate of the present invention, dispersibility and heat resistance comparable or superior to those of layered silicates organophilized with conventional organophilizing agents (quaternary ammonium salts) can be obtained.

Further, the third object of the present invention is achieved by a composition comprising the aforementioned organically modified layered silicate and an organic solvent or a composition comprising the aforementioned organically modified layered silicate and a thermoplastic resin.

The organically modified layered silicate of the present invention can be favorably dispersed and mixed in an organic solvent or a thermoplastic resin. As a result, the composition of the present invention can be used as a composite material having superior thermal stability.

BEST MODE FOR CARRYING OUT THE INVENTION

Hereafter, the tetraalkylphosphonium salt, organically modified layered silicate and composition thereof of the present invention will be described in more detail.

In the present specification, ranges indicated with "to" mean ranges including the numerical values before and after "to" as the minimum and maximum values, respectively.

[Tetraalkylphosphonium Salt of the Present Invention]

The tetraalkylphosphonium salt of the present invention has a branched alkyl chain containing 9 or more carbon atoms in total. The branched alkyl chain containing 9 or more carbon atoms in total is preferably a branched alkyl chain containing 9 to 100 carbon atoms in total, more preferably a branched alkyl chain containing 12 to 50 carbon atoms in total, further preferably a branched alkyl chain containing 16 to 36 carbon atoms in total. If the tetraalkylphosphonium salt has a branched alkyl chain containing less than 9 carbon atoms in total, hydrophobicity decreases, and therefore sufficient surface activity may not be obtained. On the other hand, if the tetraalkylphosphonium salt has a branched alkyl chain containing more than 100 carbon atoms in total, hydrophilicity markedly decreases, and therefore sufficient surface activity may not be obtained, or dispersibility may be degraded.

Specific examples of the branched alkyl chain containing 9 or more carbon atoms in total include, for example, 2-butyloctyl group, 2-hexyldecyl group, 2-octyldodecyl group, 2-decyltetradecyl group, 2-dodecylhexadecyl group, 2-tetradecyloctadecyl group, 2-hexadecylicosyl group, 3,5,5-trimethylhexyl group, 3,7-dimethyloctyl group, 3,7,11,15-tetramethylhexadecyl group and so forth. Preferred are branched alkyl chains branching at the 2-position such as 2-butyloctyl group, 2-hexyldecyl group, 2-octyldodecyl group, 2-decyltetradecyl group, 2-dodecylhexadecyl group, 2-tetradecyloctadecyl group and 2-hexadecylicosyl group. 2-Hexadecylicosyl group is more preferred. Further, the alkyl group may have an unsaturated bond (double bond or triple bond) or a substituent such as an ester group, an amide group, an ether group or a phenylene group as a partial structure.

It is sufficient that at least one of the aforementioned branched alkyl chains containing 9 or more carbon atoms in total is contained in the tetraalkylphosphonium salt. When two or more branched alkyl chains are contained, the branched alkyl chains may be identical or different. It is more preferred that one branched alkyl chain is contained. Although alkyl chains other than the branched alkyl chain are not particularly limited, they each preferably contain 4 or more carbon atoms in total, and are more preferably n-butyl groups. It is particularly preferred that all alkyl chains other than the branched alkyl chain are n-butyl groups. Since a phosphonium compound having an alkyl chain containing 3 or less carbon atoms in total has a low melting point, it may be difficult to be handled.

The tetraalkylphosphonium salt of the present invention comprises a phosphonium ion ($P^+$) having four alkyl groups and an anion ($X^-$). The anion constituting the tetraalkylphosphonium salt of the present invention is not particularly limited, and examples thereof include anions of halogen atom, p-toluenesulfonic acid, $BF_4$, $ClO_4$, $PF_6$, $NO_3$ and so forth.

The tetraalkylphosphonium salt of the present invention may comprise one kind of tetraalkylphosphonium salt or two or more kinds of tetraalkylphosphonium salts.

The tetraalkylphosphonium salt of the present invention can be obtained by reacting a trialkylphosphine with a branched alkyl halide. As the trialkylphosphine, commercially available compounds can be used. The branched alkyl halide can be synthesized by halogenating a commercially available branched alcohol. As the commercially available branched alcohol, NJCOL 160BR, NJCOL 200A, NJCOL 240A, NJCOL C32-36 (all produced by New Japan Chemical Co., Ltd.), Fine Oxocol 140, Fine Oxocol 1600, Fine Oxocol 180, Fine Oxocol 180N, Fine Oxocol 2000, Fine Oxocol 2600 (all produced by Nissan Chemical Industries Ltd.) and so forth are preferably used. However, the branched alcohol is not limited to these examples. For the method of synthesizing a branched alkyl halide from a branched alcohol, known reaction conditions can be employed. For example, a method comprising bromination using phosphorus tribromide, a method comprising bromination using carbon tetrabromide and triphenylphosphine and so forth can be mentioned.

As reaction conditions for the reaction of the obtained branched alkyl halide and a trialkylphosphine, reaction conditions used in known synthesis methods can be employed. Examples thereof include a method of reacting a branched alkyl halide and trialkylphosphine by heating in the absence of a solvent and so forth.

Specific examples of the tetraalkylphosphonium salt of the present invention will be shown below. However, the tetraalkylphosphonium salt of the present invention is not limited to these compounds.

[Organically Modified Layered Silicate of the Present Invention]

The organically modified layered silicate of the present invention contains the aforementioned tetraalkylphosphonium salt having at least one branched alkyl chain having 9 to 100 carbon atoms in total between layers of a layered silicate as an organophilizing agent.

Although the layered silicate usable in the organically modified layered silicate of the present invention is not particularly limited, clay minerals, hydrotalcite compounds and other similar compounds having swelling property and/or cleavage property are particularly preferred. Examples of such clay minerals includes kaolinite, dickite, nacrite, halloysite, antigorite, chrysotile, pyrophyllite, montmorillonite, beidellite, nontronite, saponite, sauconite, stevensite, hectorite, tetrasilylic mica, sodium taeniolite, muscovite, margarite, talc, vermiculite, phlogopite, xanthophyllite, chlorite and so forth.

The layered silicate may be either a natural substance or synthesized substance. The layered silicates may be used in each kind, or two or more kinds of them may be used together.

Shape of the aforementioned layered silicate is not particularly limited. However, if a lot of layers of the layered silicate are stacked, cleavage of the layered silicate becomes difficult after organophilization thereof. Therefore, thickness of the layered silicate not organophilized is preferably a thickness of one layer (about 1 nm) as far as possible. The average length thereof is 0.01 to 50 μm, preferably 0.05 to

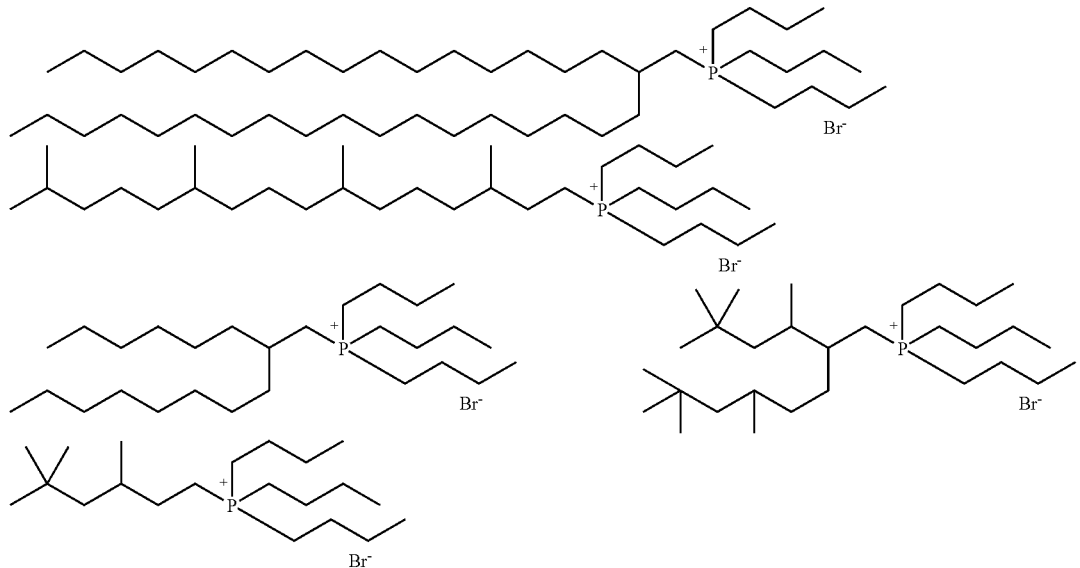

Since the tetraalkylphosphonium salt of the present invention has a hydrophilic/lipophilic balance comparable to that of a quaternary ammonium salt having two long-chain alkyl groups, it can be preferably used as a surfactant for forming lamellar liquid crystals or bilayer membrane vesicles in water. This characteristic indicates that the tetraalkylphosphonium salt of the present invention is useful as a dispersing agent for pigment, phase transfer catalyst etc. in water or an organic solvent, a surfactant exhibiting ultra low interfacial tension in a water/oil system and so forth.

10 μm, and a layered silicate having an aspect ratio of 20 to 500, preferably 50 to 200, can be preferably used.

The aforementioned layered silicate has ion-exchangeable inorganic cations between layers. The ion-exchangeable inorganic cations mean metal ions such as those of sodium, potassium and lithium existing on crystal surfaces of the layered silicate. These ions exhibit a property that they can be exchanged for a cationic substance, and preferred are layered silicates that can be inserted (intercalated) with various substances having a cationic property between the layers of the layered silicate.

The aforementioned organophilizing agent is considered to exist on the surfaces and between layers of the organically modified layered silicate. In particular, its existence between layers can be easily confirmed by analyzing the expansion of interlayer spacing of the organophilized layered silicate using X-rays.

Although the cation exchange capacity (CEC) of the aforementioned layered silicate is not particularly limited, it is preferably 10 to 200 meq/100 g, more preferably 50 to 150 meq/100 g, further preferably 90 to 130 meq/100 g. If the cation exchange capacity of the layered silicate is less than 10 meq/100 g, amount of cationic substance (tetraalkylphosphonium salt) to be inserted (intercalated) between layers of the layered silicate by ion exchange becomes small, and therefore the layers may not be sufficiently organophilized for each other. On the other hand, if the cation exchange capacity exceeds 200 meq/100 g, bonding strength between layers of the layered silicate becomes too strong. Thus, cleavage of crystal leaves becomes difficult.

Specific examples of the layered silicate satisfying the aforementioned requirements include Sumecton SA produced by Kunimine Industries, Kunipia F produced by Kunimine Industries, Somasif ME-100 produced by CO-OP Chemical, Lucentite SWN produced by CO-OP Chemical and so forth.

Although the method for incorporating the tetraalkylphosphonium salt of the present invention between layers of the layered silicate is not particularly limited, a method of incorporating the tetraalkylphosphonium salt by exchanging inorganic cations for the tetraalkylphosphonium salt of the present invention through an ion exchange reaction is preferred in view of ease of synthesis operation.

The method for ion exchange of the ion-exchangeable inorganic cations of the layered silicate for the tetraalkylphosphonium salt having at least one branched alkyl chain containing 9 or more carbon atoms in total is not particularly limited, and a known method can be used.

Specifically, methods of performing ion exchange in water, ion exchange in alcohol, ion exchange in a mixed solvent of water and alcohol and so forth can be used. For example, as for the ion exchange in water, an operation of adding a layered silicate to an aqueous solution obtained by uniformly dissolving a tetraalkylphosphonium salt having at least one branched alkyl chain containing 9 or more carbon atoms in total in water to perform ion exchange can be mentioned. For the ion exchange in water, although the mixing ratio of the tetraalkylphosphonium salt having at least one branched alkyl chain containing 9 or more carbon atoms in total and water is not particularly limited, it is preferably in the range of 1:1 to 1:10000, more preferably 1:10 to 1:1000, further preferably 1:20 to 1:200. The ion exchange is preferably performed at a temperature in the range of 0 to 100° C., more preferably at a temperature in the range of 10 to 90° C., further preferably at a temperature in the range of 20 to 80° C. Further, after completion of the reaction, the ion-exchanged layered silicate can be isolated by removing the solvent, unreacted raw materials and byproduct inorganic salts by filtration.

Progress of the aforementioned ion exchange can be confirmed by a known method. For example, by using a method of confirming exchanged inorganic ions in the filtrate by ICP emission spectrometry, a method of confirming expansion of the interlayer spacing of the layered silicate by X-ray analysis, a method of confirming existence of organic compounds on the basis of decrease in weight during a temperature rising process by using a thermobalance, exchange of ion-exchangeable inorganic ions in the layered silicate for a tetraalkylphosphonium salt having a branched alkyl chain containing 9 or more carbon atoms in total can be confirmed. The ion exchange is preferably performed for 0.05 equivalent (5%) or more, more preferably 0.1 equivalent (10%) or more, further preferably 0.5 equivalent (50%) or more, of the equivalents of the ion-exchangeable inorganic ions in the layered silicate.

[Composition of the Present Invention]

Hereafter, the composition of the present invention will be explained. The composition of the present invention is a composition comprising the organically modified layered silicate of the present invention and an organic solvent or a thermoplastic resin.

The organic solvent contained in the composition of the present invention is not particularly limited so long as it has affinity for the organically modified layered silicate of the present invention. Examples of such an organic solvent include aromatic hydrocarbons such as benzene, toluene and xylene; ethers such as ethyl ether, tetrahydrofuran, diglyme and methyl cellosolve; ketones such as acetone, methyl ethyl ketone, methyl isobutyl ketone and cyclohexanone; aliphatic hydrocarbons such as n-pentane, n-hexane, n-octane, cyclohexane and squalane; alcohols such as methanol, ethanol, propanol and isopropanol; halogenated hydrocarbons such as carbon tetrachloride, chloroform, dichloromethane, 1,2-dichloroethane, perchloroethylene and chlorobenzene; esters such as ethyl acetate, dibutyl phthalate and dioctyl phthalate; amides such as dimethylformamide; sulfoxides such as dimethyl sulfoxide and so forth.

Although the contents of the organically modified layered silicate and the organic solvent in the composition of the present invention are not particularly limited, the proportion of the organically modified layered silicate in the organic solvent is preferably 0.01 to 30% (w/v), further preferably 0.1 to 10% (w/v).

Further, the composition of the present invention may be a composition comprising the organically modified layered silicate and a thermoplastic resin. The thermoplastic resin contained in the composition of the present invention is not particularly limited so long as it has a decomposition starting temperature comparable to or lower than that of the organically modified layered silicate, and known thermoplastic resins can be used. Specific examples include polyethylene (PE), polypropylene (PP), polybutadiene, polymethylpentene, cycloolefin polymer, polystyrene (PS), acrylonitrile/butadiene/styrene copolymer (ABS), styrene/anhydrous maleic acid copolymer, polyvinyl chloride (PVC), polyethylene terephthalate (PET), polyethylene naphthalate (PEN), polymethyl methacrylate (PMMA), nylon 6, nylon 6,6, cellulose acetate (TAC), polycarbonate (PC), modified polyphenylene ether (m-PPE), polyphenylene sulfide (PPS), polyether ketone (PEK), polyether ether ketone (PEEK), polysulfone (PSF), polyether sulfone (PES), polyphenylene sulfide (PPS), liquid crystal polymer (LCP) and so forth.

Although the method for dispersing the organically modified layered silicate in a thermoplastic resin is not particularly limited, the following two kinds of methods are preferred. That is, the first method is a method of kneading a thermoplastic resin and the organically modified layered silicate at a temperature equal to or higher than the melting point of the thermoplastic resin. The second method is a method of uniformly dissolving a thermoplastic resin in an organic solvent, then adding the organically modified layered silicate dispersed in the organic solvent to the above solvent, sufficiently mixing them with stirring and then evaporating the organic solvent to disperse the organically modified layered silicate in the thermoplastic resin.

The layered silicate organophilized with the tetraalkylphosphonium salt of the present invention and a composition thereof can be utilized in various fields. For example, a composition comprising the organically modified layered silicate of the present invention and an organic solvent can improve rheological characteristics of the organic solvent. Therefore, the composition of the present invention can be suitably used as a dispersion medium for cosmetics, pharmaceuticals, dyes, pigments, ultraviolet absorbers etc. Further, the composition of the present invention can be used in the form of thin film formed by coating and drying the composition of the present invention.

Further, the composition comprising the organically modified layered silicate of the present invention and a thermoplastic resin can be utilized as a composite material superior in mechanical characteristics, electrification property, gas barrier property, antibacterial property and so forth. In particular, such a composition can be suitably used as a plastic plate having high heat resistance.

A film formed by using the composition of the present invention (hereinafter referred to as "this film") can contain other components (for example, additives such as antistatic agents) in addition to the composition of the present invention. This film can be obtained by making the composition of the present invention into a shape of film by a usual method such as a melt extruding method, calender method, or solution casting method. Further, this film may be monoaxially or biaxially stretched. In order to further improve adhesion to a coated layer, this film may be subjected to surface treatment such as corona discharge treatment, glow discharge treatment, UV treatment or plasma treatment.

Although thickness of this film can be suitably determined depending on its use, it is preferably in the range of 10 to 300 µm, further preferably in the range of 50 to 250 µm. If the thickness is less than 10 µm, strength becomes insufficient, and handling of the film becomes difficult. If the thickness is greater than 300 µm, transparency and flexibility tend to be degraded.

A substrate containing this film can be used as, for example, a substrate for display device, a substrate for electronic circuit or the like. When the substrate containing this film is used as a substrate for display device, electrodes, dielectric layer, protective layer, partitions, fluorophore and so forth can be formed on this film to obtain a member for display device, and displays such as PDP, PALC, FED and VFD can be further produced by using the member. When the substrate containing this film is used as a substrate for electronic circuit, a circuit can be formed on this film to produce an electronic circuit used for various kinds of electronic equipments and semiconductor devices. Further, a substrate containing this film can be used as a substrate for solar cell, electronic paper, other various products aiming at portable use and so forth.

Furthermore, an image display device having this film can be utilized as a liquid crystal device, organic EL device or the like. The organic EL device is preferably used according to any of the embodiments described in Japanese Patent Laid-Open Publication (Kokai) Nos. 11-335661, 11-335368, 2001-192651, 2001-192652, 2001-192653, 2001-335776, 2001-247859, 2001-181616 and 2001-181617, Japanese Patent Application Nos. 2001-58834, 2001-58835, 2001-89663 and 2001-334858.

That is, this film can be used as a base material film and/or a protective film in an organic EL device having this film.

EXAMPLES

The present invention will be further specifically explained with reference to the following examples of the present invention. The materials, amounts, ratios, types and procedures of treatments and so forth shown in the following examples can be suitably changed unless such changes depart from the spirit of the present invention. Accordingly, the scope of the present invention should not be construed as limited to the following specific examples.

Examples 1, 2 and Comparative Examples 1 to 4

These examples relate to an ammonium salt having a branched alkyl group (Compound 7) and tetraalkylphosphonium salts having a branched alkyl group (Compounds 8 to 12).

1. Preparation and Identification of Tetraalkylphosphonium Salts a. Synthesis of Compound 1

A branched alkyl halide group as the raw material of Compound 1 was synthesized by brominating hydroxyl groups of NJCOL C32-36 (produced by New Japan Chemical Co., Ltd.) by using carbon tetrabromide and triphenylphosphine. In an amount of 2500 g (5 mol) of NJCOL C32-36 was suspended in 5 L of THF and added with 1759 g (5.3 mol) of carbon tetrabromide. Further, 1391 g (5.3 mol) of triphenylphosphine was added porsionwise under water cooling. Then, the mixture was stirred for 7 hours and left standing overnight at room temperature, and the precipitates were separated by filtration. THF was evaporated from the filtrate, and then the residue was recrystallized from 2-propanol and hexane. The crystals were dried at room temperature to obtain 2236 g of the objective halide (yield: 79%).

In an amount of 58 g (0.1 mol) of this compound and 25 ml (0.1 mol) of 33% trimethylamine ethanol solution (ACROS) were stirred at room temperature for 30 days, and the precipitates were collected by filtration. The resulting solids were recrystallized to obtain 19 g of Compound 1 (yield: 30%, white solid).

b. Synthesis of Compound 2

A branched alkyl halide group as the raw material of Compound 2 was synthesized in the same manner as that used for Compound 1. In an amount of 200 g (0.36 mol) of the obtained halide of NJCOL C32-36 and 89 ml of tributylphosphine (0.36 mol, produced by Tokyo Kasei Kogyo) were reacted at 100° C. for 30 hours under nitrogen. The reaction mixture was cooled to room temperature and then added with ethyl acetate, and the insoluble matters were removed by filtration. Ethyl acetate was evaporated from the filtrate, and the residue was purified by silica gel column chromatography and vacuum dried to obtain 94 g of Compound 2 (yield: 34%, transparent oil).

c. Synthesis of Compound 3

A branched alkyl halide group as the raw material of Compound 3 was synthesized by brominating hydroxyl groups of Fine Oxocol 1800 (produced by Nissan Chemical Industries Ltd.) using phosphorus tribromide. In an amount of 1622 g (6 mol) of Fine Oxocol 1800 was added dropwise with 812 g (3 mol) of phosphorus tribromide at room temperature. Then, the reaction temperature was raised to 70 to 80° C., and the mixture was stirred. Completion of the reaction was confirmed by TLC, and hexane and water were added. The mixture was extracted, and the extract was washed and then distilled to obtain 1960 g of a compound (halide, yield: 98%).

In an amount of 6.7 g (20 mmol) of this compound and 5 ml (20 mmol) of tributylphosphine were reacted at 90° C. for 37 hours under nitrogen. The reaction mixture was purified by silica gel column chromatography to obtain 3.3 g of Compound 3 (yield: 31%, pale yellow oil).

d. Synthesis of Compound 4

1-Bromo-2-ethylhexane (produced by Tokyo Kasei Kogyo) and tributylphosphine (produced by Tokyo Kasei Kogyo) were reacted in the same manner as that used for Compound 3, and the product was purified to obtain 3.3 g of Compound 4 (yield: 42%).

e. Identification of Compounds

Whether Compounds 1 to 4 synthesized above had the objective structures was confirmed by using $^1$H-NMR, $^{31}$P-NMR and FAB-MS. Data from NMR and FAB-MS are shown below.

<Compound 1>

$^1$H-NMR . . . /ppm (TMS, CDCl$_3$) 0.88 (t, 6H), 1.8-1.2 (m, 61H), 3.40 (d, 2H), 3.50 (s, 9H)

<Compound 2>

$^1$H-NMR . . . /ppm (TMS, CDCl$_3$) 0.97 (t, 6H), 0.99 (t, 9H), 1.37-1.8 (m, 73H), 2.3 (m, 2H), 2.5 (m, 6H)

<Compound 3>

$^{31}$P-NMR . . . /ppm (85% H$_3$PO$_4$, CD$_3$OD) 39.4, 60.6 FAB-MS (Negative) m/z=615.4 ([M]+[Br—])

<Compound 4>

$^1$H-NMR . . . /ppm (TMS, CDCl$_3$) 1.0 (m, 15H), 1.2-1.8 (m, 21H), 2.3-2.6 (m, 8H) $^{31}$P-NMR . . . /ppm (85% H$_3$PO$_4$, CD$_3$OD) 38.8 FAB-MS (Negative) m/z=475.2 ([M]+[Br—])

f. Compounds 5 and 6

As Compound 5 and 6, products purchased from Tokyo Kasei Kogyo were used as they were.

The structures of Compounds 1 to 6 are shown below.

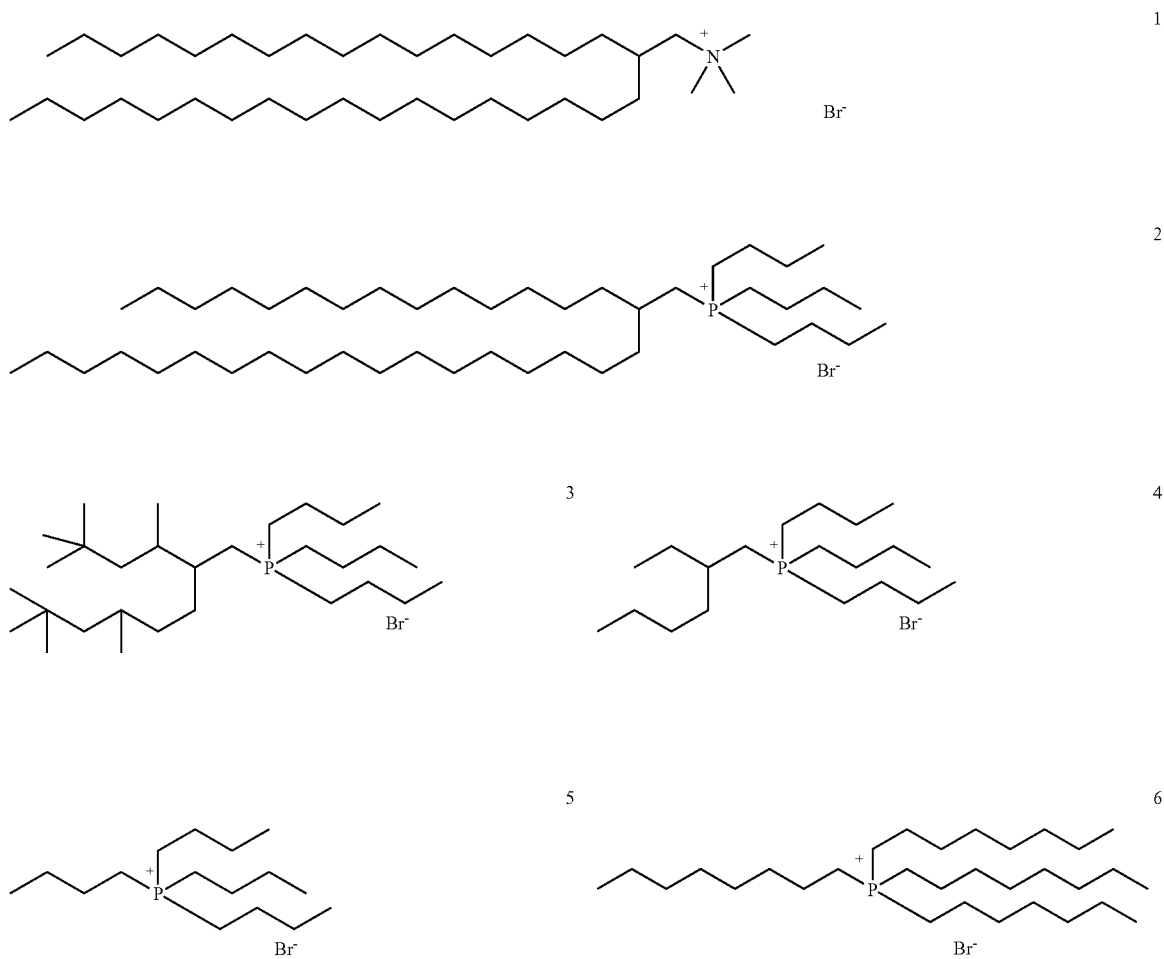

2. Preparation of Organically Modified Layered Silicate

Each of Compounds 1 to 6 (2.5 g each) as an organophilizing agent was completely dissolved in a mixed solvent of water and isopropyl alcohol (250 g, the proportion of water was changed up to 20 to 80% by weight depending on solubility of the organophilizing agent) at room temperature, then added with 2.5 g of swellable synthetic mica (ME-100, produced by CO-OP Chemical) or natural montmorillonite (Kunipia F, produced by Kunimine Industries Co., Ltd.) and stirred at 80° C. for 1 hour. After completion of the reaction, the solvent, unreacted raw materials and byproduct inorganic salts were removed by filtration, and the residue was further sufficiently washed with a mixed solvent of water and isopropyl alcohol having the same composition as that of the reaction solvent to isolate an organically modified layered silicate.

3. Measurement of Interlayer Spacing and Dispersibility of Organically Modified Layered Silicates Interlayer spacings of the obtained 12 kinds of organically modified layered silicates were determined by measuring X-ray diffraction at room temperature for the range of 2θ=1.2 to 30° according to the θ-2θ method using RINT-2500 produced by Rigaku Corporation and CuKα rays as a radiation source. As for dispersibility in chloroform and cyclohexane, the obtained 12 kinds of layered silicates (0.25 g each) were finely pulverized, placed in a glass sample bottle together with chloroform (20.0 g) or cyclohexane (10.0 g), subjected to ultrasonic irradiation for 10 minutes and left standing overnight, and then the dispersibility was macroscopically evaluated. The obtained results are shown in Table 1.

The weight changes of 15 to 26 occurred when the temperature was raised at 30° C./min for the range of 25 to 600° C. under argon atmosphere were measured by using Thermo Plus System produced by Rigaku Corporation. Decomposition starting temperature was defined as a temperature at which weight of an organophilizing agent decreased by 1%. The obtained results are shown in Table 1.

As shown in Table 1, compared with the layered silicate not organophilized (Reference Example 1), expansion of interlayer spacing was observed in the layered silicates organophilized with Compounds 1 to 5 (Examples 1, 2 and Comparative Examples 1 to 3). This indicates that the organophilizing agent was intercalated between layers of the layered silicates. On the other hand, when Compound 6 was used as an organophilizing agent (Comparative Example 4), no expansion of interlayer spacing was observed. This indicates that the layered silicate was not organophilized.

Further, when the layered silicates were compared for dispersibility by dispersing them in organic solvents, it was revealed that the layered silicates organophilized with Compounds 1 to 3 having a branched alkyl chain containing 9 or more carbon atoms in total (Examples 1 and 2) had superior dispersibility in the organic solvents in comparison with the layered silicate not organophilized (Reference Example 1), layered silicate organophilized with Compound 4 having a branched alkyl group containing 8 or less carbon atoms in total (Comparative Example 2) or layered silicate organophilized with Compound 5 having a straight alkyl group (Comparative Example 3).

Further, the layered silicates were compared for thermal stability. The layered silicates organophilized with Compounds 2 and 3 having an alkyl chain containing 9 or more carbon atoms in total (Examples 1 and 2) had superior thermal stability in comparison with the layered silicate organophilized with Compound 1 containing a quaternary ammonium salt (Comparative Example 1).

The above examples, comparative examples and reference example showed that the layered silicates of the present invention organophilized with a tetraalkylphosphonium salt having a branched alkyl chain containing 9 or more carbon atoms in total had both of superior dispersibility and superior thermal stability.

As described above, the tetraalkylphosphonium salt of the present invention has surface activity and thermal stability comparable or superior to those of conventional cationic surfactants. Further, since the organically modified layered silicate of the present invention contains a tetraalkylphosphonium compound having at least one branched alkyl chain containing 9 or more carbon atoms in total between layers, it can organophilize layered silicates to a degree comparable to that obtainable with conventional organophilizing agents, and have thermal stability and dispersibility superior to those of the conventional organophilizing agents. Since the

TABLE 1

| Sample | Layered silicate | Organo-philizing agent | Interlayer spacing | Dispersibility in organic solvent | | Decomposition starting temperature |
|---|---|---|---|---|---|---|
| | | | | Chloroform | Cyclohexane | |
| Example 1 | ME-100 | Compound 2 | 4.4 nm | ◎ | ◎ | 270° C. |
| | Kunipia F | Compound 2 | 3.6 nm | ◎ | ◎ | 270° C. |
| Example 2 | ME-100 | Compound 3 | 2.6 nm | ○ | ○ | 260° C. |
| | Kunipia F | Compound 3 | 2.3 nm | ○ | ○ | 260° C. |
| Comparative Example 1 | ME-100 | Compound 1 | 3.0 nm | ◎ | ◎ | 170° C. |
| | Kunipia F | Compound 1 | 3.2 nm | ◎ | ◎ | 170° C. |
| Comparative Example 2 | ME-100 | Compound 4 | 1.8 nm | Δ | Δ | 270° C. |
| | Kunipia F | Compound 4 | 1.9 nm | Δ | Δ | 270° C. |
| Comparative Example 3 | ME-100 | Compound 5 | 1.7 nm | X | X | 290° C. |
| | Kunipia F | Compound 5 | 1.7 nm | X | X | 290° C. |
| Comparative Example 4 | ME-100 | Compound 6 | 1.0 nm | X | X | — |
| | Kunipia F | Compound 6 | 1.0 nm | X | X | — |
| Reference Example 1 | ME-100 | None | 1.0 nm | X | X | — |
| | Kunipia F | None | 1.0 nm | X | X | — |

◎: Uniform dispersion,
○: Dispersion with supernatant,
Δ: Swelled precipitates,
X: Unswelled precipitates composition of the present invention contains the aforementioned organically modified layered silicate, the Theological characteristics are improved, and it can be used as a composite material having superior mechanical characteristic, electrification property, gas barrier property and antibacterial property.

The present disclosure relates to the subject matter contained in Japanese Patent Application No. 090670/2003 filed Mar. 28, 2003, which is expressly incorporated herein by reference in its entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A tetraalkylphosphonium salt having at least one branched alkyl chain containing 12 to 100 carbon atoms in total.

2. The tetraalkylphosphonium salt according to claim 1, wherein said branched alkyl chain contains 12 to 50 carbon atoms in total.

3. The tetraalkylphosphonium salt according to claim 1, wherein said branched alkyl chain contains 16 to 36 carbon atoms in total.

4. The tetraallkylphosphonium salt according to claim 1, wherein said branched alkyl chain branches at the 2-position.

5. The tetraalkylphosphonium salt according to claim 4, wherein said branched alkyl chain is 2-hexadecylicosyl group.

6. The tetraalkylphosphonium salt according to claim 1, wherein alkyl chains other than said branched alkyl chain each contains 4 or more carbon atoms in total.

7. The tetraalkylphosphonium salt according to claim 1, wherein alkyl chains other than said branched alkyl chain are the same.

8. The tetraalkylphosphonium salt according to claim 7, wherein alkyl chains other than said branched alkyl chain are n-butyl group.

9. The tetraalkylphosphonium salt according to claim 1, which comprises an anion selected from the group consisting of anions of halogen atom, p-toluenesulfonic acid, $BF_4$, $ClO_4$, $PF_6$ and $NO_3$.

* * * * *